United States Patent [19]

Kamber

[11] Patent Number: 4,603,120

[45] Date of Patent: Jul. 29, 1986

[54] CYCLIC OCTAPEPTIDES AND PHARMACEUTICAL PREPARATIONS THEREOF, AS WELL AS PROCESSES FOR THEIR MANUFACTURE, AND THEIR USE

[75] Inventor: Bruno Kamber, Arlesheim, Switzerland

[73] Assignee: Ciba-Geigy Corporation, Ardsley, N.Y.

[21] Appl. No.: 451,630

[22] Filed: Dec. 20, 1982

[30] Foreign Application Priority Data

Dec. 24, 1981 [CH] Switzerland ................. 8282/81

[51] Int. Cl.$^4$ ................. A61K 37/24; C07K 7/26
[52] U.S. Cl. ................. 514/11; 530/328; 530/317; 530/323
[58] Field of Search ................. 260/112.5 R; 514/15, 514/16, 11

[56] References Cited

U.S. PATENT DOCUMENTS 4,238,481 12/1980 Rink et al. ................. 260/112.5 S

OTHER PUBLICATIONS

*Chemical Abstracts*, 85, 571 (1976), abs. no. 85:783672.
*Chemical Abstracts*, 95, 711 (1981), abs. no. 95:98330s.
Parsons, *Drug Design*, vol. 2, Academic Press, Inc., New York, 337 (1971).
Parson, *Peptide Hormones*, University Park Press, Baltimore, Chapter 1, p. 6.
Brazeau et al., Science, vol. 179, pp. 77–79 (1973).

*Primary Examiner*—Delbert R. Phillips
*Assistant Examiner*—F. T. Moezie
*Attorney, Agent, or Firm*—Bruce M. Collins; Karl F. Jorda; Michael W. Glynn

[57] ABSTRACT

Cyclic octapeptides of the formula

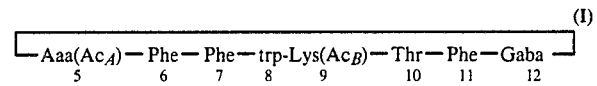

in which
Aaa represents a radical of a straight-chained α,ω-diaminoalkanoic acid having from 4 to 7 carbon atoms,
trp represents a radical L-Trp or, especially, D-Trp, or a radical derived therefrom, which carries a halogen atom in the indole nucleus,
Ac$_A$ represents an acyl radical Ac of an optionally substituted carboxylic acid which is positioned at the ω-amino group, or represents an amidino group or hydrogen, and
Ac$_B$ represents an acyl radical Ac$^1$ of an amino acid or of an oligopeptide which is positioned at the ε-amino group, or, preferably, represents hydrogen,
as well as physiologically tolerable salts and therapeutically acceptable complexes thereof can be used as antidiabetics and for the treatment of gastro-intestinal bleeding in an analogous manner to somatostatin. They can be obtained by conventional processes of peptide chemistry, especially by the cyclization of corresponding linear peptides.

11 Claims, No Drawings

CYCLIC OCTAPEPTIDES AND PHARMACEUTICAL PREPARATIONS THEREOF, AS WELL AS PROCESSES FOR THEIR MANUFACTURE, AND THEIR USE

The invention relates to novel cyclopeptides of the somatostatin type and processes for their manufacture, and also to pharmaceutical preparations containing these compounds and the use of these compounds or preparations for therapeutic purposes.

The invention relates especially to cyclopeptides that have the most essential features of somatostatin, such as the partial sequence of amino acids 6–11, but not the two sulphur-containing cysteine radicals. The somatostatin-analogous cyclopeptides according to the invention include cyclic octapeptides of the formula

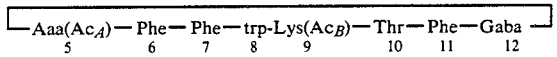
(I)

in which
  Aaa represents a radical of a straight-chained α,ω-diaminoalkanoic acid having from 4 to 7 carbon atoms,
  trp represents a radical L-Trp or, especially, D-Trp, or a radical derived therefrom, which carries a halogen atom in the indole nucleus,
  $Ac_A$ represents an acyl radical Ac of an optionally substituted carboxylic acid which is positioned at the ω-amino group, or represents an amidino group or hydrogen, and
  $Ac_B$ represents an acyl radical $Ac^1$ of an amino acid or of an oligopeptide which is positioned at the ε-amino group, or, preferably, represents hydrogen,
and salts and complexes thereof.

As is known, somatostatin, a cyclic tetradecapeptide of the formula

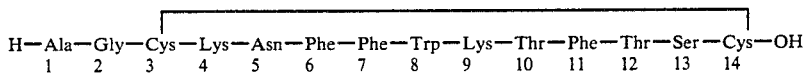

[Science 179, 77 (1973)], inhibits the pituitary-controlled secretion of the somatotropic hormone (somatotropin). It also inhibits the secretory activity of the endocrine pancreas, such as the secretion of insulin and glucagon. In the case of somatostatin itself, these valuable properties cannot be used fully in practice since this compound has too short a duration of action. In addition, it is often of advantage if the active ingredient exercises its inhibitory effect mainly on one of the two glands while the other gland should be affected as little as possible. (In most cases, the inhibition of pituitary secretion, i.e. of somatotropic hormone release, is less desirable). For this reason, attempts are being made to achieve a dissociation of the inhibitory effects by modifying the basic sequence, especially by omitting individual original amino acids and/or exchanging them for other, often also "unnatural", amino acids, and to achieve as long a duration of action as possible. It has been found, for example, that especially advantageous physiological properties of this type occur in cyclopeptides of the type

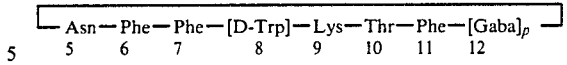
(M)

in which
  Gaba represents the radical of γ-aminobutyric acid, and
  p represents the number 0, 1 or 2,
and in other closely related compounds, cf. our U.S. Pat. No. 4,238,481. A typical feature of these compounds is the presence of a straight carbon chain which is intended to simulate the original grouping —CH₂—S—S—CH₂— in the cysteine radical of somatostatin.

Surprisingly it has now been found that by a very unusual modification of the basic structure of this simple active ingredient of the formula M, i.e. by the exchange, not hitherto used in the case of somatostatin analogues, of the asparagine radical in the 5-position for the radical of an α-amino acid that carries an optionally modified amino group at the terminal carbon atom, an analogue is produced in which the original activity of the basic structure M is not only retained but is often further increased and heightened in the sense discussed above, especially in relation to the intensity of action and duration of action. Such a result is all the more surprising since it is generally assumed that a substituent of the type of the terminal amino group in the radical of the amino acid which is introduced by way of exchange may cancel the biological activity of the original active ingredient as a result of its predominantly basic character, or steer it in a completely different direction. For example, in the determination of the insulin and glucagon release using the isolated, perfused, arginine-stimulated pancreas of a rat [method according to B. Petrack, A. J. Czernik, W. Itterly, J. Ansell and H. Chertock: Biochem. and Biophys. Res. Commun. 73, 934 –939 (1976)], it was found that the [Lys⁵,D-Trp⁸,Gaba¹²]-cyclo-somatostatin-(5–12)-octapeptide exerts an inhibitory effect on insulin and glucagon secretion that is greater by a factor of from 5 to 10 compared with [D-Trp⁸,Gaba¹²]-cyclo-somatostatin(5–12)-octapeptide of the above formula M (p=1).

A radical of an α,ω-diaminoalkanoic acid, indicated by the symbol Aaa in formula I, is derived from the basic structure of butyric acid or oenanthic acid (heptanoic acid), but preferably valeric acid or, especially, caproic acid (hexanoic acid) and is incorporated into the peptide ring by way of the α-amino group. This preferably has the same steric arrangement as the naturally occurring α-amino acids of the L-series. There come into consideration as especially preferred radicals having a free terminal ω-amino group ($Ac_A$=hydrogen), those of L-ornithine and especially of L-lysine, and also of D-lysine; special mention should also be made of analogous radicals in which the terminal ω-amino group is functionally modified within the scope of the meaning of $Ac_A$, for example is substituted by the amidino group NH₂—C(=NH)—(such as, especially, in the arginine radical) or by an acyl radical Ac, especially an acyl radical Ac¹ derived from an α-amino acid or from an oligopeptide, for example one of those given special mention hereinafter.

In the initially defined compounds of the formula I, trp preferably represents D-Trp, but also an L- or D-Trp radical, which carries in the indole nucleus, especially in the 5-position, a halogen atom, such as chlorine or, especially, fluorine: for example especially [D-(5F)Trp], which is derived from D-5-fluorotryptophan.

In the initially defined compounds of the formula I, γ-aminobutyric acid is indicated by the symbol Gaba.

If, in the formula I, the symbol $Ac_A$ or $Ac_B$ represents hydrogen, this means that the terminal amino group of the $Aaa^5$ or $Lys^9$ radical, respectively, is free.

The carboxylic acid forming the basis of the acyl radical Ac is, for example, an alkanecarboxylic acid which, when unsubstituted, preferably contains a maximum of 18 carbon atoms and, when substituted, preferably a maximum of 8 carbon atoms. The substituents are, on the one hand, hydroxyl, mercapto, lower alkylmercapto, such as methylmercapto, guanidino, carboxyl and carboxamido, and also amino groups, or an imino group bonded to 2 different carbon atoms and, on the other hand, mono- or bi-cyclic hydrocarbyl or heterocyclyl radicals, such as, especially, phenyl, p-hydroxyphenyl, 1- or 2-naphthyl, 2-, 3- or 4-pyridyl, 2- or 3-indolyl, 2- or 4-imidazolyl, 2-, 4- or 5-thiazolyl, 2-thienyl or 2-furyl. The acid may carry one or more of the same or different substituents, the total number of carbon atoms, including the carbon-containing substituents, preferably being no more than 18. Especially preferred are acyl radicals derived from single-branched or, especially, from straight-chained, unsubstituted alkanemonocarboxylic acids containing a maximum of 18, preferably a maximum of 9, carbon atoms, such as acetic, propionic, butyric, isobutyric, valeric, isovaleric, caproic, oenanthic, undecanoic, lauric, myristic, palmitic and stearic acid.

Of the acyl radicals Ac there are preferred the radicals of α-amino acids indicated by the symbol Ac¹, especially those that are derived from alkanecarboxylic acids having a maximum of 7 carbon atoms and that, in addition to the amino group, may also carry the above-mentioned substituents. Of these there are especially preferred those radicals that are derived from naturally occurring, especially as peptide building blocks, α-amino acids of the L-series and their closely related analogues, such as, especially, the enantiomers of the "unnatural" D-series. Of the preferred α-amino acids there come into consideration, for example, more especially the following: glycine, alanine, valine, leucine, isoleucine, phenylalanine, aspartic acid, glutamic acid, arginine, histidine and, especially, lysine, and also α-aminobutyric acid, norvaline, isovaline, norleucine, ornithine and citrulline, as well as, also, asparagine, glutamine, tyrosine, tryptophan, methionine, threonine, serine and, more especially, also proline and hydroxyproline (in which the α-amino group is closed to form a ring by the alkyl radical). As radicals Ac¹ there also come into consideration oligopeptide radicals, especially di- and tri-peptide radicals. These are preferably constructed from the naturally occurring α-amino acids (above all those given special mention above, such as, especially, lysine or proline). Preferably, the radical of one amino acid is repeated several times in the oligopeptide chain, such as, for example, in the H-Lys-Lys-Lys- or other analogously constructed dipeptide and tripeptide acyl radicals.

There may be mentioned as preferred radicals -Aaa-(Ac¹)-, for example:

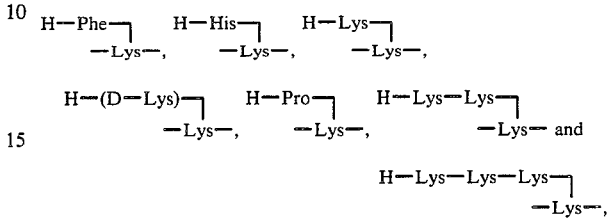

and also analogously constructed radicals in which, instead of one or more lysine radicals (equally, whether in the form of the radical Aaa of the exchange amino acid and/or a constituent of the acyl radical Ac¹), there is an ornithine radical. (The symbols used above signify, in accordance with the current nomenclature rules, that the lower radical, that is -Lys-, is substituted in the side chain, that is at the ε-amino group, by the upper acyl radical, for example H-Pro- or H-Lys-Lys-Lys-).

Especially preferred cyclooctapeptides of the formula I according to the invention are, for example, the following:

[Lys⁵,D-Trp⁸,Gaba¹²]-cyclo-somatostatin(5-12)octapeptide of the formula

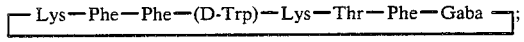

[Orn⁵,D-Trp⁸,Gaba¹²]-cyclo-somatostatin(5-12)octapeptide of the formula

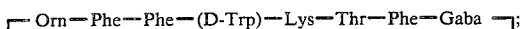

[Nε-(Pro)-Lys⁵,D-Trp⁸,Gaba¹²]-cyclo-somatostatin(-5-12)-octapeptide of the formula

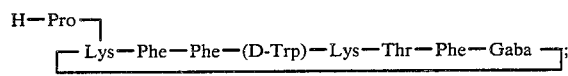

[Nε-(Lys⁵,D-Trp⁸,Gaba¹²)-cyclo-somatostatin(5-12)-octapeptide of the formula

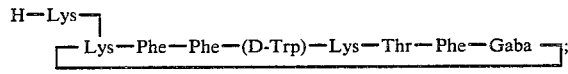

[Nε-(Phe)-Lys⁵,D-Trp⁸,Gaba¹²]-cyclo-somatostatin(-5-12)-octapeptide of the formula

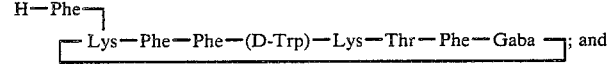

[Nε-(Lys-Lys-Lys)-Lys⁵, D-Trp⁸,Gaba¹²]-cyclo-somatostatin(5-12)octapeptide of the formula

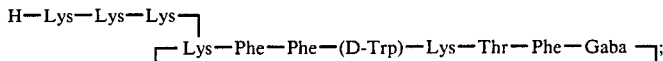

as well as, also

[Nδ-(Pro)-Orn⁵,D-Trp⁸,Gaba¹²]-cyclo-somatostatin(-5-12)-octapeptide,

[Nδ-(Orn)-Orn⁵,D-Trp⁸,Gaba¹²]-cyclo-somatostatin(-5-12)-octapeptide,

[Nδ-(His)-Orn⁵,D-Trp⁸,Gaba¹²]-cyclo-somatostatin(-5-12)-octapeptide, or

[Lys⁵,D-(5F)Trp⁸,Gaba¹²]-cyclo-somatostatin(5-12)octapeptide.

Those of the cyclopeptides of the formula I characterised above either in a general manner or as being preferred that contain a free amino group or amidino group may also be in the form of acid addition salts. There come into consideration as acid addition salts especially physiologically tolerable salts with customary therapeutically acceptable acids; of the inorganic acids there may be mentioned hydrohalic acids (such as hydrochloric acid), but also sulphuric acid and phosphoric or pyrophosphoric acid, and of the organic acids there may be mentioned especially sulphonic acids (such as benzenesulphonic or p-toluenesulphonic acid or lower alkanesulphonic acids, such as methanesulphonic acid), as well as, also, carboxylic acids, such as acetic acid, lactic acid, palmitic and stearic acid, malic acid, tartaric acid, ascorbic acid and citric acid. Those of the cyclopeptides characterised by the formula I that contain in the radicals Ac$_A$ and/or Ac$_B$ a free carboxyl group, which gives acidic character to the entire cyclopeptide, may also be in the form of salts, for example sodium, potassium, calcium or magnesium salts, or also ammonium salts derived from ammonia or a physiologically tolerable organic nitrogen-containing base. Those of the compounds of the formula I that contain both a free carboxyl group and a free amino group (or amidino group) may also be in the form of internal salts.

The peptides of the formula I according to the invention may alternatively be in the form of complexes. Complexes should be understood as being compounds of which the structures have not yet been fully clarified and that are formed when certain inorganic or organic substances are added to peptides and that impart to these a prolonged action. Such substances are described, for example, for ACTH and other adrenocorticotropically active peptides. There may be mentioned, for example, inorganic compounds that are derived from metals, such as calcium, magnesium, aluminium, cobalt and, especially, zinc, especially sparingly soluble salts, such as phosphates, pyrophosphates and polyphosphates, as well as hydroxides of these metals, and also alkali metal polyphosphates, for example "Calgon ® N", "Calgon ® 322", "Calgon ® 188" or "Polyron ® 12". Organic substances that prolong action are, for example, non-antigenic types of gelatin (for example polyoxygelatin), polyvinylpyrrolidone and carboxymethylcellulose, also sulphonic or phosphoric acid esters of alginic acid, dextran, polyphenols and polyalcohols, especially polyphloretin phosphate and phytic acid, and also polymers and copolymers of basic or, especially, acidic amino acids, for example protamine or polyglutamic acid.

Unless otherwise indicated, the short forms of the amino acid radicals refer to radicals of the α-amino acids of the naturally occurring L-series. To illustrate, in the formulae the radical of D-tryptophan is indicated by -(D-Trp)-.

Unless otherwise indicated, the term "lower", wherever it appears in connection with an organic radical or compound, indicates such a radical or compound having a maximum of 7 carbon atoms, but preferably a maximum of 4 carbon atoms.

The novel cyclopeptides according to the invention have a physiological action that is fundamentally similar to the action of somatostatin. They can therefore be used advantageously in therapeutic indications similar to those of somatostatin, for example especially for the treatment of functional disorders in which the secretion of the somatotropic hormone or of glucagon is abnormally high, such as in the case of acromegalia or diabetes. As, in addition to this, they inhibit loss of blood in the gastrointestinal tract, they can also be used successfully in that range of indications.

The cyclopeptides according to the invention are obtained using conventional manufacturing processes of peptide chemistry that are known per se They are manufactured, for example, by cyclising a linear peptide corresponding to the cyclopeptide, that is to say cyclising such a peptide that has the same amino acids in the same sequence as the cyclic peptide according to the invention, wherein, however, an amide bond between any two adjacent ring-forming amino acids is interrupted and is replaced by corresponding terminal functional groups, i.e. a carboxyl and an amino group, which may also be present in an activated form.

The compounds according to the invention are produced by cyclisation, especially by cyclising a corresponding linear peptide of the formula $$H\text{-}[I_a]\text{-}V \qquad \text{(II)}$$

in which $I_a$ represents a radical corresponding to the formula I in which the amide bond between any two adjacent amino acid radicals of the peptide ring is interrupted, and V represents a free hydroxyl group, a hydroxyl group modified by an activating group or represents the hydrazino group —NH—NH₂, wherein amino, carboxyl and hydroxyl groups which may be present that are not participating in the cyclisation reaction are temporarily in protected form and are subsequently liberated and, if desired, free amino groups present in a resulting cyclopeptide are acylated, if necessary with temporary protection of any hydroxyl and remaining amino groups present.

Of the linear peptides of the formula II, those in which the radical Gaba or especially the radical Aaa represents a terminal amino acid in the radical $[I_a]$ are preferred. An especially preferred starting material is characterised by the formula $$H\text{-Aaa}(Ac_a)\text{-Phe-Phe-trp-Lys}(Ac_b)\text{-Thr-Phe-Gaba-}V \qquad \text{(IIa)}$$

in which Ac$_a$ represents the above-characterised acyl radical Ac or a ω-amino-protecting group $X_o$, and Ac$_b$ represents the above-characterised acyl radical of an α-amino acid or of an oligopeptide $Ac^1$ or represents a ω-amino-protecting group $X_o$, Aaa and trp have the meanings mentioned at the beginning and V has the meanings given directly above. (The temporary protection of carboxyl, hydroxyl and amino groups during the cyclisation applies also to the corresponding groups in the radicals Ac and $Ac^1$).

A functional group represented by the symbol V supplements the carbonyl group of the C-terminal amino acid radical and forms together with that group a free carboxyl group, an activated ester group or the carbazolyl group, as the case may be.

The activating group by which the hydroxyl group is modified is especially one that forms the activated ester of N-hydroxysuccinimide, 1-hydroxybenzotriazole, N,N'-dicyclohexylisourea, 2,4,5-trichlorophenol, 2-nitrophenol, 4-nitrophenol, pentachlorophenol or pentafluorophenol but may also be a different activating group of this type known from peptide chemistry, cf. Houben-Weyl, volume 15/II.

The cyclisation according to the invention of the linear peptides of the formula II or IIa is carried out in a manner known per se by means of conventional coupling methods used for the formation of the amide bond, the peptide starting materials, however, being used in a very low concentration in order to influence the course of the coupling operation in favour of intramolecular cyclisation at the expense of intermolecular polycondensation.

The linear peptides are advantageously used in an approximately $1.10^{-4}$-molar to approximately $1.10^{-2}$-molar concentration, preferably an approximately $1.10^{-3}$-molar concentration, which corresponds to a weight/volume concentration of approximately 0.01 to 1.0%, preferably 0.1%. The reaction mixture can be correspondingly diluted from the start, or this dilution can be produced continuously by the slow dropwise addition of the starting material, and optionally the other reagents, to the reaction mixture.

Cyclisation is preferably carried out, at a starting concentration indicated above, by (a) treating a starting material of the formula II in which V represents a free hydroxyl group and in which remaining amino, carboxyl and hydroxyl groups present are temporarily protected, with a carbodiimide, optionally in the presence of an active ester-forming component, or (b) reacting with an organic base a starting material of the formula II in which V represents a hydroxyl group modified to form the activated ester and the terminal α-amino group is present in protonated form, at least the amino and carboxyl groups present that are not participating in the cyclisation being protected, or (c) first treating a starting material of the formula II in which V represents the group —NH—NH$_2$ and at least the amino groups present that are not participating in the cyclisation are protected, with nitrous acid or a lower alkyl ester thereof under acidic conditions and then cyclising with excess organic base at an above-mentioned low concentration.

A carboxyl group is protected by a protecting group W in the manner described hereinafter. Advantageously, the groups $X_o$ and $X_a$ or Y, as defined hereinafter, are used for the protection of the amino and hydroxyl groups.

The cyclisation is carried out in suitable solvents, for example dioxan, tetrahydrofuran, acetonitrile, pyridine, dimethylformamide, dimethylacetamide, dimethyl sulphoxide, N-methylpyrrolidone, hexamethylphosphoric acid triamide, and also chloroform, methylene chloride and ethyl acetate, and mixtures thereof.

In process variant (a) the cyclisation is brought about by a carbodiimide, preferably N,N'-dicyclohexylcarbodiimide, which is advantageously used in excess; it is to be assumed that the starting material of the formula II having a free carboxyl group is first converted into an activated ester of dicyclohexylisourea (or an analogous isourea) and this active ester formed in situ immediately reacts further. The intermediate formation of an active ester can doubtless be considered by the addition of an active ester-forming component as an auxiliary reagent; for this purpose, active ester-forming components customary in peptide chemistry may be used, such as, especially, 2,4,5-trichlorophenol, 2- or 4-nitrophenol, pentachlorophenol and pentafluorophenol, but above all N-hydroxy compounds, among which N-hydroxysuccinimide, N-hydroxypiperidine and above all 1-hydroxybenzotriazole are especially advantageous. In this variant, the operating temperature is generally from 0° to 70°, preferably from 35° to 55°.

In variant (b) which is carried out with ready-prepared active esters, especially those already pointed out, cyclisation takes place spontaneously as the terminal α-amino group is deprotonated by the organic base. The bases used are preferably quaternary, or especially tertiary, amines, for example triethylamine or N-ethylmorpholine. The operation is preferably carried out at from 10° to 30°, especially at room temperature.

In variant (c), the first phase, i.e. the formation of the acid azide by treating with nitrous acid or an ester thereof, may advantageously be carried out at a considerably higher concentration of the starting materials than in the case of the subsequent cyclisation. The operation is advantageously carried out with approximately one equivalent of a lower alkyl nitrite, such as ethyl nitrite, isoamyl nitrite and, especially, tert.-butyl nitrite, in a hydrochloric acid medium at temperatures of from approximately $-30°$ to approximately $-5°$, preferably approximately $-20°$; a slight excess of nitrite is permissible. The solution of the azide formed is then, after the necessary dilution, rendered basic at a temperature of from approximately 0° to approximately 35° by means of excess organic base, for example one of those mentioned above, and thereby made to cyclise spontaneously as in the case of process variant (b).

Narrower selection of the protecting groups depends on the specific purpose and, especially when several functional groups are to be protected, for example in the radicals $Ac_A$ and $Ac_B$, expedient combinations must be selected.

As ω-amino-protecting groups $X_o$ there may be used any of the amino-protecting groups customarily used in peptide chemistry, as described synoptically in the corresponding reference works, for example in Houben-Weyl: Methoden der organischen Chemie, 4th edition, volume 15/I; E. Wünsch (editor): Synthese von Peptiden, (Georg Thieme Verlag, Stuttgart; 1974). Thus, for example, the acyl groups derived from sulphurcontaining organic acids, such as organic sulphonic acids (such as p-toluenesulphonyl, and also benzenesulphonyl and o-nitrophenylsulphenyl groups), but especially carboxylic acid acyl radicals, may be used. Such an acyl radical to be used as protecting group differs fundamentally from the above-characterised acyl radical Ac by the fact that it can be removed selectively from the ω-amino group carrying it, thus freeing the amino group, whilst the peptide basic structure remains undamaged, whereas an acyl radical Ac cannot be removed from the ω-amino group without at the same time having a detrimental effect on the peptide amide bond.

The carboxylic acid acyl radicals indicated by the symbol $X_o$ that can be used as ω-amino-protecting groups are, for example, formyl, trifluoroacetyl or phthaloyl, but especially radicals that are derived from carbonic acid and, specifically, from monoesters thereof. These are especially acyl radicals that can be removed by acidolysis, such as especially the radicals of the type tert.-butoxycarbonyl, such as tert.-amyloxycarbonyl, isopropoxycarbonyl, diisopropylmethoxycarbonyl, allyloxycarbonyl, cyclopentyloxycarbonyl, cyclohexyloxycarbonyl, d-isobornyloxycarbonyl and adamantyloxycarbonyl as well as, also, certain aralkoxycarbonyl radicals of the 2-(p-biphenylyl)-2-propoxycarbonyl type, which are described in Swiss Patent Specification No. 509 266. Furthermore, there are included among the acyl radicals $X_o$ also acyl radicals that can be removed by reduction or by means of a base, for example especially those of the benzyloxycarbonyl type, such as benzyloxycarbonyl itself and derivatives thereof, which are substituted in the aromatic moiety by halogen atoms, nitro groups, lower alkoxy groups and/or lower alkyl radicals, such as p-chloro- and p-bromobenzyloxycarbonyl, p-nitrobenzyloxycarbonyl, p-methoxybenzyloxycarbonyl, p-tolyloxycarbonyl and, especially, 4-pyridylmethoxycarbonyl. An especially advantageous acyl radical $X_o$ is an ethoxycarbonyl radical that carries in the β-position a silyl group substituted by 3 hydrocarbon radicals, such as a triphenylsilyl, a dimethyl-butyl-silyl or, especially, a trimethylsilyl group. A β-(trihydrocarbylsilyl)-ethoxycarbonyl radical of this type, such as a β-(tri-lower alkylsilyl)ethoxycarbonyl radical, for example especially β-(trimethylsilyl)-ethoxycarbonyl, forms together with the ω-amino group to be protected a corresponding β-trihydrocarbylsilylethoxycarbonylamino group (for example the β-trimethylsilylethoxycarbonylamino group). Although this radical is stable under the conditions of acidic hydrolysis and of hydrogenolysis, it can be removed by the action of fluoride ions under quite specific, very mild conditions. In this respect it behaves analogously to the β-silylethyl ester group described below as a carboxyl-protecting group. (This similarity must be given particular consideration when synthesising; except for isolated cases, the use of one of these protecting groups precludes the simultaneous use of the other protecting group). Further details are given hereinafter in the description of the protection of the carboxyl group by a β-silylethyl ester. Finally, there also come into consideration as $X_o$, groups of the aralkyl type that can be removed by acidolysis, such as benzhydryl and triphenylmethyl (trityl).

There may be used as hydroxyl-protecting groups Y any of the groups conventionally used for this purpose in peptide chemistry, cf. the work cited above (HoubenWeyl). Groups that can be removed by acidolysis, such as 2-tetrahydropyranyl and most especially tert.-butyl, and also tert.-butoxycarbonyl, are preferred. It is, however, also possible to use hydroxyl-protecting groups that can be removed by reduction or by means of bases, for example benzyl and benzyloxycarbonyl groups, which may be substituted in the aromatic moiety by halogen, nitro and/or lower alkoxy, or lower alkanoyl radicals, such as acetyl, or aroyl radicals, such as benzoyl. If certain limiting measures are observed, it is also possible to proceed without protecting the hydroxyl groups.

There may be used as the carboxyl-protecting group W any group customarily used for this purpose, cf. the above-cited work (Houben-Weyl). Thus, carboxyl groups are protected, for example, by the formation of hydrazides or by esterification. Suitable for esterification are, for example, lower optionally substituted alkanols, such as methanol, ethanol, cyanomethyl alcohol, 2,2,2-trichloroethanol, benzoylmethyl alcohol and especially tert.-butyl alcohol, or alternatively an optionally substituted benzyl alcohol. An especially advantageous category of substituted alkanols is ethyl alcohols that carry in the β-position a tri-substituted silyl group, such as a triophenylsilyl, a dimethyl-butyl-silyl or, especially, a trimethylsilyl group. As described, for example, in Belgian Patent Specification No. 851,576, these alcohols are especially suitable for protecting carboxyl groups because, although the corresponding β-silylethyl esters, for example β-(trimethylsilyl)-ethyl ester, have the stability of customary alkyl esters, they can be removed selectively under mild conditions by the action of fluoride ions while all the other protecting groups are retained.

Preferably, the protecting groups $X_o$, Y and W are so selected that they can be removed under similar conditions; especially preferred are the groups that can be removed by acidolysis that have already been given special mention. The removal of all of these protecting groups is, then, advantageously carried out in a single operation; it is also possible, however, to use groups of a different kind and for each to be removed individually. If, for example, an end product of the formula I in which $Ac_A$ and $Ac_B$ are different is to be produced by subsequent acylation of a liberated amino group of the radical $Aaa^5$ or $Lys^9$, respectively, both protecting groups $X_o$ in the radicals $Ac_a$ and $Ac_b$ are so selected that one of them can be removed whilst the other, and preferably also the protecting groups W and especially Y that are present, are retained. In this case, first of all the first (in most case more stable) protecting group $X_o$ is selectively removed and the liberated amino group is acylated, then the second amino group is liberated and, if desired, also acylated. The protecting groups W and especially Y are advantageously so selected that they are not removed until in the final phase, that is to say after the last acylation. Such combinations of amino-protecting groups which can be removed selectively with respect to each other (and also in relation to other protecting groups of the type W and Y) are generally known and customary in peptide chemistry, for example groups that can be removed by reduction, on the one hand, and groups that can be removed by acidolysis, on the other hand.

Removal of the protecting groups is carried out in the generally known manner; acid hydrolysis (acidolysis) is carried out, for example, by means of trifluoroacetic acid, hydrochloric acid or hydrogen fluoride, in the case of acid-sensitive protecting groups also by means of a lower aliphatic carboxylic acid, such as formic acid and/or acetic acid, in the presence of water and optionally a polyhalogenated lower alkanol or lower alkanone, such as 1,1,1,3,3,3-hexafluoropropan-2-ol or hexafluoroacetone. The groups that can be removed by reduction, especially those that contain benzyl radicals, are preferably removed by hydrogenolysis, for example by hydrogenation with palladium catalysis. The 4- pyridylmethoxycarbonyl group is preferably removed by reduction using zinc.

The subsequent acylation of free amino groups present in radicals Aaa[5] and/or Lys[9] of the cyclopeptide, which is to be carried out if desired, may preferably be carried out with temporary protection of a free hydroxyl group present. The acylation is carried out especially by treating a resulting cyclopeptide of the formula

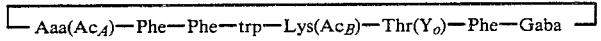 (III)

$$\lfloor\ \text{Aaa}(Ac_A)\text{—Phe—Phe—trp—Lys}(Ac_B)\text{—Thr}(Y_o)\text{—Phe—Gaba}\ \rfloor$$

in which $Y_o$ represents hydrogen or a hydroxyl-protecting group Y of the meaning described in more detail above and trp, Aaa, $Ac_A$ and $Ac_B$ have the abovedefined meaning with the proviso that at least one of the radicals $Ac_A$ and $Ac_B$ is hydrogen, and amino and/or hydroxyl groups present in the other radical are temporarily protected, with a carboxylic acid $Ac_OOH$, in which $Ac_O$ represents a radical corresponding to the above-defined radicals Ac or $Ac^1$ in which amino and hydroxyl groups present may carry protecting groups $X_o$, $X_a$ and Y, or with a reactive derivative of such an acid and, if desired or necessary, liberating amino groups or hydroxyl groups in the resulting product by removing the protecting groups $X_o$, $X_a$ and Y.

The meaning of the symbol $X_a$, which indicates an α-amino-protecting group, is described in detail hereinafter in the synthesis of the peptide chain. Preferably, similar protecting groups are used both in the radical $Y_o$ and the radical $Ac_O$ and are removed at the same time following the acylation reaction.

A reactive derivative of the acid $Ac_OOH$ is, for example, an anhydride, especially a symmetrical anhydride of the formula $Ac_O$—O—$Ac_O$ or a mixed anhydride with a different organic acid, for example with trifluoroacetic acid, or especially with an inorganic acid, for example an acid azide or acid halide, especially an acid chloride. A reactive acid derivative is preferably an activated ester, for example one in which the acid $Ac_OOH$ is esterified with 2,4,5-trichlorophenol, pentachlorophenol, pentafluorophenol, 2-nitrophenol or, especially, 4-nitrophenol, or with an N-hydroxy compound, such as N-hydroxysuccinimide, 1-hydroxybenzotriazole or N-hydroxypiperidine, or with an N,N'-disubstituted isourea, such as especially N,N'-dicyclohexylisourea or a similar activating component known from peptide chemistry, cf. Houben-Weyl: Methoden der organischen Chemie; 4th edition, vol 15/I and II, E. Wünsch (editor): Synthese von Peptiden (Georg Thieme Verlag, Stuttgart; 1974).

The acylation is carried out in a manner known per se, preferably in customary solvents, for example dioxan, tetrahydrofuran, acetonitrile, pyridine, dimethylformamide, dimethyl acetamide, and also chloroform and methylene chloride, and in expedient mixtures thereof. It is also possible for the reaction to be carried out with an addition of an organic base, for example a quaternary or, especially, tertiary amine, such as triethylamine, N-ethylmorpholine or N-methylpiperidine, in order to maintain the amino group to be acylated in deprotonated form. The reaction temperature is usually from −20° to +70° C., preferably from approximately 0° C. to room temperature.

In general, active esters are especially advantageous as acylating agents since they acylate amino groups preferentially to hydroxyl groups and therefore make the protection of hydroxyl groups practically superfluous. In order to avoid undesired O-acylation, usually only one equivalent of the acylating agent is used. If, however, for any reason it is more advantageous to dispense with selective acylation, as may be the case especially in the reaction with acid chlorides, the acylating agent is used in excess and the simultaneously acylated hydroxyl groups are subsequently liberated in the same conventional manner as the protected hydroxyl groups, especially by basic hydrolysis, for example with sodium or potassium hydroxide in the presence of water.

Those of the end products according to the invention that contain basic groups are obtained, depending on the nature of isolation, as bases or as acid addition salts; these can subsequently be converted one into the other in a manner known per se. Analogously, end products with acidic groups may also be in the form of salts, it being possible for both forms to be converted one into the other in known manner.

Also the formation of the above-mentioned complexes is carried out according to known methods; complexes with sparingly soluble metal compounds, for example aluminium or zinc compounds, are produced preferably in an analogous manner to ACTH, for example by reaction with a soluble salt of the particular metal, for example zinc chloride or zinc sulphate, and precipitation with an alkali metal phosphate and/or hydroxide. Complexes with organic compounds, such as polyoxygelatine, carboxymethylcellulose, polyvinylpyrrolidone, polyphloretin phosphate, polyglutamic acid, etc. are obtained by mixing these substances with the peptide in aqueous solution. In the same manner insoluble compounds can also be produced with alkali metal polyphosphates.

The starting materials of the above-characterised formula II, and the intermediates used for the synthesis thereof and described in the Examples, are novel and some of them can also be used with advantage for the synthesis of other somatostatin analogues, for example those with analogous amino acid partial sequences. The present invention relates to these starting materials and intermediates and to processes for their manufacture. They are obtained according to methods known per se, by condensing with one another amino acids or smaller peptide units necessary for their synthesis to form CO—NH bonds in any time sequence, it being possible for functional groups not participating in the reaction to be temporarily protected.

In the manufacture of these starting materials, as well as all the necessary intermediates, there come into consideration as protecting groups for the terminal α-amino and carboxyl groups especially the protecting groups customary in the synthesis of long-chained peptides, which can be removed readily and selectively, for example by solvolysis or reduction. They have already been mentioned several times hereinbefore under the designations $X_a$ and W.

There may be mentioned as α-amino-protecting group $X_a$, for example: optionally substituted (for example by halogen, nitro, lower alkyl or lower alkoxy) di- or tri-aryl-lower alkyl groups (such as diphenylmethyl or triphenylmethyl groups, for example benzhydryl, trityl, di-(p-methoxy)-benzhydryl) or especially groups that are derived from carbonic acid and that can be removed by hydrogenolysis, such as benzyloxycarbonyl groups optionally substituted in the aromatic radical by halogen atoms, nitro groups, lower alkyl or lower alkoxy groups [for example benzyloxycarbonyl (i.e. carbobenzoxy), p-bromo- or p-chloro-benzyloxycarbonyl, p-nitrobenzyloxycarbonyl, p-methoxybenzyloxycarbonyl]; also 2-(p-biphenylyl)-2-propoxycarbonyl and similar aryloxycarbonyl groups described in Swiss Patent Specification No. 509 266. It must be ensured that the $\alpha$-amino-protecting group $X_a$ can be removed selectively while the $\omega$-amino-protecting groups $X_o$ of the radicals $Aaa^5$ and $Lys^9$ are retained. It is, moreover, advantageous if, during the removal of the $\alpha$-amino-protecting groups, an optionally present carboxyl- or hydroxyl-protecting group W or Y also remains undamaged.

The carboxyl-protecting groups for this purpose are the same as those mentioned above for the corresponding meaning of the symbol W; preferably, it should be possible also to remove these selectively whilst retaining other protecting groups of a different kind.

The protecting group $X_a$ can be removed in known manner. For example, a benzyloxycarbonyl group can be removed by hydrogenolysis and the N-trityl group by mineral acids, such as hydrohalic acids (for example hydrogen fluoride or, preferably, hydrogen chloride), or by an organic acid (such as formic acid, acetic acid, chloroacetic acid or trifluoroacetic acid) in aqueous or absolute trifluoroethanol as the solvent (cf. German Offenlegungsschrift DT No. 2 346 147), or by aqueous acetic acid; the tert.-butoxycarbonyl group is removed, for example, by trifluoroacetic acid or hydrochloric acid, and the 2-(p-biphenylyl)isopropoxycarbonyl group by aqueous acetic acid or, for example, by a mixture of glacial acetic acid, formic acid (82.8 % strength) and water (7:1:2) or in accordance with the process indicated in DT 2 346 147.

The $\beta$-silylethyl ester groups are preferably removed by reagents yielding fluoride ions, for example fluorides of quaternary organic bases, such as tetraethylammonium fluoride. However, they can also be removed, like the conventional alkyl esters, by alkaline hydrolysis, for example by means of alkali metal hydroxides, carbonates or bicarbonates, or they can be converted by hydrazinolysis, for example by means of hydrazine hydrate, into the corresponding carbozoyl groups. Acidolysis is preferably used to remove tert.-butyl esters and hydrogenolysis for benzyl esters.

The condensation of the amino acid units and/or peptide units to be carried out in order to manufacture the starting materials of the formula II is effected in a manner known per se, preferably by linking an amino acid or a peptide having a protected $\alpha$-amino group and a free or activated terminal carboxyl group (=active component) to an amino acid or peptide having a free $\alpha$-amino group and a free or, preferably, protected (for example esterified) terminal carboxyl group (=passive component). In the resulting product, the terminal amino group is liberated and this peptide, containing a free $\alpha$-amino group and an optionally protected terminal carboxyl group, is reacted again with a further active component, i.e. an amino acid or a peptide having an activated terminal carboxyl group and a protected $\alpha$-amino group, etc. The carboxyl group can be activated, for example, by converting into an acid azide, anhydride, imidazolide, isoxazolide or an activated ester, such as one of those mentioned hereinafter, or by reaction with a carbodiimide, such as N,N'-dicyclohexylcarbodiimide, [and, if desired, with the addition of N-hydroxysuccinimide or an unsubstituted or a substituted (for example halogen-, methyl- or methoxy-substituted) 1-hydroxybenzotriazole or 4-hydroxybenzo-1,2,3-triazine-3-oxide]or especially N-hydroxy-5-norbornene-2,3-dicarboximide, or by reaction with N,N'-carbonyldiimidazole. The most usual coupling method is the carbodiimide method, and also the azide method, the activated esters method and the anhydride method, the Merrifield method and the method using N-carboxyanhydrides or N-thiocarboxyanhydrides. For the formation of activated esters, as mentioned above, there are suitable, for example, phenols and thiophenols that are optionally substituted by electron-attracting substituents, such as phenol, thiophenol, thiocresol, p-nitrothiophenol, 2,4,5- and 2,4,6-trichlorophenol, pentachlorophenol, o- and p-nitrophenol, 2,4-dinitrophenol and p-cyanophenol, and also, for example, N-hydroxysuccinimide, N-hydroxyphthalimide and N-hydroxypiperidine.

In an especially preferred method of manufacturing the peptides of the formula II, the coupling method used is the carbodiimide method with N,N'-dicyclohexylcarbodiimide in the presence of 1-hydroxybenzotriazole. The terminal carboxyl group is in the form of the $\beta$-(trimethylsilyl)-ethyl ester and the $\alpha$amino group of the active component is protected in each case by the benzyloxycarbonyl group, which is removed by hydrogenolysis after each coupling step. In order to protect the $\omega$-amino group in the radical $Aaa^5$ and $Lys^{9,}$ as well as all amino groups in the radicals Ac and $Ac^{1,}$ acylation with the tert.-butoxycarbonyl group is advantageously used and to protect the hydroxyl group of the threonine radical etherification with the tert.-butyl group is advantageously used. These two protecting groups may, if desired, be removed finally in one step by acid hydrolysis, for example by means of trifluoroacetic acid, hydrochloric acid or hydrogen fluoride. If the $\omega$-amino group of the radical $Aaa^5$ or $Lys^9$ is from the start acylated by Ac or $Ac^1$, it requires no protection.

Depending on the method used, the compounds of the formula II, depending on their character, are obtained in the form of bases or acid addition salts, or in the form of acids or their salts. The bases can be obtained from the acid addition salts in a manner known per se and, in turn, therapeutically acceptable acid addition salts can be obtained from the bases by reaction with acids, for example with those that form the above-mentioned salts. Acids and their salts are also similarly related to each other. Internal salts, in the case of compounds having a corresponding structure, are obtained by adjusting the pH to a suitable neutral point.

Owing to the close relationship between the novel compounds in free form and in the form of their salts, hereinbefore and hereinafter the free compounds shall optionally also include the salts thereof and the salts shall optionally also include the free compounds, where appropriate with regard to meaning and purpose.

The invention also relates to those forms of the process in which a compound obtainable as an intermediate at any stage of the process is used as the starting material and the remaining process steps are carried out, or in which a starting material is formed under the reaction conditions or is used in the form of a derivative, optionally a salt, thereof.

Of such forms of the process according to the invention attention is drawn in particular to those in which the end products of the initially defined formula I are manufactured by, in corresponding intermediates which can be obtained, for example, by cyclisation and in which at least one of the amino, hydroxyl and/or carboxyl groups present is in protected form, freeing these groups. This form of the process, which most generally produces a compound of the formula

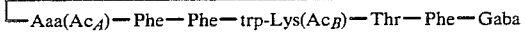

(I)

in which
- Aaa represents a radical of a straight-chained $\alpha,\omega$-diaminoalkanoic acid having from 4 to 7 carbon atoms,
- trp represents a radical L-Trp or, especially, D-Trp, or a radical derived therefrom, which carries a halogen atom in the indole nucleus,
- $Ac_A$ represents an acyl radical Ac of an optionally substituted carboxylic acid which is positioned at the $\omega$-amino group, or represents an amidino group or hydrogen, and
- $Ac_B$ represents an acyl radical $Ac^1$ of an amino acid or of an oligopeptide which is positioned at the $\epsilon$-amino group, or, preferably, represents hydrogen, or a salt or a complex thereof, is characterised in that in a structurally corresponding compound in which at least one of the amino, hydroxyl and/or carboxyl groups present carries a protecting group $X_o$, $X_a$, Y or W, any protecting groups present are removed and, if desired, a resulting basic compound is converted into an acid addition salt, or a resulting acid addition salt is converted into the corresponding base and/or a resulting compound is converted into its complex.

Preferred protecting groups $X_o$, $X_a$, Y and W have already been mentioned hereinbefore; chiefly, combinations of these are selected that can be removed under the same conditions, preferably, for example, the above-described radicals that can be removed by acidolysis (such as, especially, those of the tert.-butyl type).

In the process of the present invention, the starting materials used are preferably those that result in the compounds described at the beginning as being especially valuable.

The present invention also relates to pharmaceutical preparations that contain compounds of the formula I or pharmaceutically acceptable salts or complexes thereof. These preparations may be used especially in the above-mentioned indications if they are administered parenterally (such as intravenously, intramuscularly or subcutaneously) or also intranasally or orally. The dosage depends on the particular disorder to be treated, its severity and the duration of therapy. The number and quantity of the individual doses and also the administration scheme can best be determined on the basis of an individual examination of the patient concerned. The method of determining these factors is known to the man skilled in the art. As a rule, however, in the case of injection, a therapeutically active quantity of a compound of this type lies in the dosage range of from approximately 0.001 to approximately 0.2 mg/kg body weight. The range of from approximately 0.0015 to approximately 0.15 mg/kg body weight is preferred and administration is by intravenous infusion or subcutaneous injection. Accordingly, pharmaceutical preparations for parenteral administration in single-dose form contain per dose, depending on the type of application, from approximately 0.08 to approximately 15 mg of one of the compounds according to the invention. Apart from the active ingredient, they usually also contain a buffer, for example a phosphate buffer, that is to maintain the pH between approximately 3.5 and 7, and also sodium chloride, mannitol or sorbitol for adjusting the isotonicity. They may be in freeze-dried or dissolved form and solutions may advantageously contain an antibacterially-active preservative, for example from 0.2 to 0.3 % of 4-hydroxybenzoic acid methyl ester or ethyl ester. If the active ingredient in such preparations is to be in the form of a complex having a prolonged duration of action, then it may be formed directly by adding the complex-forming components to an injection solution that is prepared, for example, according to the abovementioned methods. A suitable additive is, for example, from 0.1 to 1.0% by weight of a zinc(II) salt (for example sulphate) in conjunction with from 0.5 to 5.0% by weight of protamine (for example as a sulphate), calculated on the total volume of the injection solution; this preparation is in the form of a solution having a pH of from 3.5 to approximately 6.5 or in the form of a suspension having a pH of from approximately 7.5 to 8.0.

A preparation for intranasal administration may be in the form of an aqueous solution or gel, an oily solution or suspension, or a fat-containing ointment. A preparation in the form of an aqueous solution is obtained, for example, by dissolving the active ingredient of the formula I, or a therapeutically acceptable salt or complex thereof, in an aqueous buffer solution having a pH of up to 7.2 and adding a substance producing isotonicity. A polymeric adhesive, for example polyvinylpyrrolidone, and/or a preservative are advantageously added to the aqueous solution. The single dose is from approximately 0.08 to approximately 15 mg, preferably from 0.25 to 10 mg, that are contained in approximately 0.05 ml of a solution or 0.05 g of a gel.

An oily form of application for intranasal administration is obtained, for example, by suspending a peptide of the formula I, or a therapeutically acceptable acid addition salt thereof, in an oil, optionally with the addition of swelling agents, such as aluminium stearate, and/or interfacially active agents (surfactants), the HLB value ("hydrophiliclipophilic balance") of which is less than 10, such as fatty acid mono-esters of polyhydric alcohols, for example glycerine monostearate, sorbitan monolaurate, sorbitan monostearate or sorbitan monooleate. A fatcontaining ointment is obtained, for example, by suspending the active ingredient according to the invention in a spreadable fat base, optionally with the addition of a surfactant having a HLB value of less than 10. An emulsion ointment is obtained by triturating an aqueous solution of the peptide active ingredient in a soft, spreadable fat base with the addition of a surfactant of which the HLB value is less than 10. All these intranasal forms of application may also contain preservatives. The single doses are from approximately 0.08 to approximately 15 mg, preferably from 0.25 to 10 mg, contained in from approximately 0.05 to approximately 0.1 g of the base substance.

Also suitable for intranasal administration are inhalation or insufflation preparations, such as insufflation capsules that permit the active ingredient to be insufflated in the form of a powder with respiratory air, or aerosols or sprays that can disperse the pharmacological active ingredient in the form of a powder or in the form of drops of a solution or suspension. Preparations having powder-dispersing properties generally contain adjuncts in addition to the active ingredient: insufflation capsules contain, for example, solid carriers, such as lactose; aerosol or spray preparations contain, for example, a liquid propellant having a boiling point of below room temperature and, if desired, other carriers, such as liquid or solid non-ionic or anionic surfactants and/or solid diluents. Preparations in which the pharmacological active ingredient is in solution contain, in addition to this, a suitable propellant and also, if necessary, an additional solvent and/or a stabiliser. Instead of the propellant, it is also possible to use compressed air, which is produced, when required, by means of a suitable compressing and releasing device.

The invention relates also to the use of the novel compounds of the formula I and therapeutically acceptable salts and complexes thereof as pharmacologically active compounds, especially in the indications mentioned at the beginning, preferably in the form of pharmaceutical preparations. The daily dose administered to a warm-blooded animal weighing approximately 70 kg is from approximately 0.1 to approximately 120 mg.

Some especially advantageous variants of putting the invention into practice are illustrated in more detail in the following Examples, but the invention is not limited thereby. Temperatures are given in degrees Centigrade; the conventional short forms, for example those compiled in "Synthese von Peptiden" (editor: E. Wünsch), volume XV of "Methoden der org. Chemie" (Houben-Weyl) (1974; G. Thieme, Stuttgart) are used as abbreviations, for example for denoting amino acids, peptides, protecting groups, etc. The following abbreviations, in particular, are used:

Boc—tert.-butoxycarbonyl
But—tert.-butyl (as ether-forming group)
OBzl—benzyloxy (as ester-forming group)
OPc—pentachlorophenoxy (as ester-forming group)
OTmse—2-(trimethylsilyl)-ethoxy (as ester-forming group)
Z—benzyloxycarbonyl (carbobenzoxy)
as well as
TLC—thin layer chromatography
DCCI—dicyclohexylcarbodiimide
DMF—dimethylformamide In TLC, unless otherwise indicated, silica gel is used as the adsorbent and the following systems are used as eluants (in proportions by volume):

| System | |
|---|---|
| 101: | n-butanol/pyridine/acetic acid/water (38:24:8:30) |
| 111B: | n-butanol/pyridine/25% aqueous ammonia/water (40:24:6:30) |
| 112A: | n-butanol/pyridine/formic acid/water (42:24:4:20) |
| 157: | chloroform/methanol/water/acetic acid (70:42:10:0.5) |
| 157A: | chloroform/methanol/water/acetic acid (90:10:1:0.5) |
| 157B: | chloroform/methanol/water/acetic acid (85:13:1.5:0.5) |
| 157G: | chloroform/methanol/water/acetic acid (88:10.5:1.0:0.5) |

EXAMPLE 1

⌐Lys—Phe—Phe—(D-Trp)—Lys—Thr—Phe—Gaba⌐

280 mg of protected octapeptide of the formula

⌐Lys(Boc)—Phe—Phe—(D-Trp)—Lys(Boc)—Thr(But)—Phe—Gaba⌐ are dissolved at 5° under $N_2$ in 1.5 ml of a mixture of 89% by volume of trifluoroacetic acid, 10% by volume of water and 1% by volume of thioglycolic acid, the solution is immediately heated to 25° and, after 90 minutes at room temperature under $N_2$, precipitated with 15 ml of ether. The resulting crude trifluoroacetate of the end product is dried in vacuo, dissolved in 5 ml of 1N acetic acid and filtered through 15 ml of anion exchanger, for example AG ®1-X8 (a product of Bio-Rad Laboratories, Richmond, Calif., USA) in acetate form. The eluate is concentrated by evaporation in vacuo and the residue is subjected to countercurrent distribution over 680 stages in the system tert.-amyl alcohol/acetic acid/water/toluene (4:2:5:0.8). The phases contained in the units 180 to 220 (K=0.4) are collected, concentrated by evaporation in vacuo and lyophilised from tert.-butanol/water (1:1).

The resulting title compound is uniform in two systems according to thin layer chromatography.

TLC: system 157: $R_f$0.4. system 157G: $R_f$0.6.

The peptide starting material can be obtained in the following manner

Stage 1.1 Z-Lys(Boc)-Phe-Phe-OH 4.19 g of Z-Lys(Boc)-OPc and 2.47 g of HCl.H-Phe-Phe-OH are taken up in 50 ml of dimethylformamide, 0.84 ml of N-ethylmorpholine are added and the whole is left to stand for 24 hours at 20°. The reaction mixture is concentrated by evaporation and the residue is triturated with water and dried over phosphorus pentoxide. Recrystallisation from ether yields crystals having a melting point of 154° to 156°.

TLC: system 157 A: $R_f$0.25

Stage 1.2
Z-Lys(Boc)-Phe-Phe-(D-Trp)-Lys(Boc)-Thr(But)-Phe-OTmse 460 mg of 1-hydroxybenzotriazole and 680 mg of DCCI are added to a solution of 2.1 g of Z-Lys(Boc)-Phe-Phe-OH (stage 1.1) and 2.51 g or H-(D-Trp)-Lys(-boc)-Thr(But)-Phe-OTmse in 35 ml of dimethylformamide and the mixture is left at room temperature for 15 hours. For working up, the precipitated dicyclohexylurea is removed by filtration and the filtrate is concentrated by evaporation in a high vacuum. The oily residue is triturated with 5 ml of methanol and filtered with suction. The undissolved material is, in order to purify it, triturated again with 5 ml of methanol at 50°, filtered with suction, washed with methanol and dried in vacuo. The product is uniform according to TLC.

TLC: system (chloroform/methanol 9:1): $R_f$0.73

Stage 1.3
Z-Lys(Boc)-Phe-Phe-(D-Trp)-Lys(Boc)-Thr(But)-Phe-OH 2.93 g of Z-Lys(Boc)-Phe-Phe-(D-Trp)-Lys(Boc)-Thr(But)-Phe-OTmse (stage 1.2) are dissolved in 75 ml of a freshly produced anhydrous 0.15M tetraethylammonium fluoride solution in dimethylformamide and maintained at 25° for 30 minutes. The reaction mixture is cooled to 5°, 2.0 ml of 1N aqueous hydrochloric acid are added while stirring well, and the product is precipitated by the addition of 700 ml of water. The material filtered off is washed with water, dried in vacuo over phosphorus pentoxide and further used directly.

TLC: system 157 A: $R_f$ 0.30

Stage 1.4
Z-Lys(Boc)-Phe-Phe-(D-Trp)-Lys(Boc)-Thr(But)-Phe-Gaba-OBzl 286 mg of 1-hydroxybenzotriazole, 385 mg of DCCI and 0.255 ml of N-ethylmorpholine are added to a mixture of 2.17 g of Z-Lys(Boc)-Phe-Phe-(D-Trp)-Lys(Boc)-Thr(But)-Phe-OH (stage 1.3) and 740 mg of Gaba-benzyl ester p-toluene sulphonate in 16 ml of dimethylformamide and the mixture is left at room temperature for 20 hours. For working up, 10 ml of ice-cold methanol are added to the mixture which is then filtered. The resulting solid is, in order to be purified further, stirred for 10 minutes with 5 ml of warm methanol, the suspension is cooled to 0°, and the pure product is filtered off and dried in vacuo.

TLC: [chloroform/methanol (95:5)]: $R_f$ 0.55

Stage 1.5
H-Lys(Boc)-Phe-Phe-(D-Trp)-Lys(Boc)-Thr(But)-Phe-Gaba-OH

A solution of 2.04 g of Z-Lys(Boc)-Phe-Phe-(D-Trp)-Lys(Boc)-Thr(But)-Phe-Gaba-OBzl (stage 1.4) in 100 ml of dimethylformamide is, after the addition of 500 mg of palladium-on-carbon (10%), hydrogenated for 6 hours at room temperature and normal pressure. For working up, the solution is concentrated to 2 ml in a high vacuum once the catalyst has been filtered off, and the product is precipitated with 25 ml of peroxide-free ether, filtered off and dried in vacuo. The crude product is subjected to the next stage 1.6 (cyclisation) without being further purified.

Stage 1.6

⌐Lys(Boc)—Phe—Phe—(D-Trp)—Lys(Boc)—Thr(But)—Phe—Gaba⌐

A solution of 630 mg of crude H-Lys(Boc)-Phe-Phe-(D-Trp)-Lys(Boc)-Thr(But)-Phe-Gaba-OH (stage 1.5), 650 mg of 1-hydroxybenzotriazole and 875 mg of DCCI in 240 ml of dimethylformamide is maintained at 50° for 20 hours. For working up, the solvent is evaporated off in a high vacuum at approximately 30°, and the residue is triturated with 10 ml of ethyl acetate. The precipitated dicyclohexylurea is removed by filtration, the filtrate is diluted to 50 ml with ethyl acetate, washed three times with 20 ml of 1N aqueous oxalic acid each time and then with water until neutral, dried over sodium sulphate and concentrated by evaporation in vacuo. The crude product is chromatographed over a column of 50 g of silica gel (used in ethyl acetate/petroleum ether 1:1). After a first run of 750 ml of ethyl acetate/petroleum ether 1:1, 500 ml of ethyl acetate elute 410 mg of the product which is uniform according to thin layer chromatography.

TLC: system 157 A: $R_f$ 0.45

EXAMPLE 2

└—Orn—Phe—Phe—(D-Trp)—Lys—Thr—Phe—Gaba—┘

1.3 g of protected octapeptide of the formula

└—Orn(Boc)—Phe—Phe—(D-Trp)—Lys(Boc)—Thr(But)—Phe—Gaba—┘ are dissolved at 5° under $N_2$ in 30 ml of a mixture of 89% by volume of trifluoroacetic acid, 10% by volume of water and 1% by volume of thioglycolic acid, the solution is immediately heated to 25° and, after 90 minutes at room temperature under $N_2$, precipitated with 100 ml of ether. The resulting crude trifluoroacetate of the end product is dried in vacuo, dissolved in 20 ml of 1N acetic acid and filtered through 40 ml of anion exchanger, for example AG®1-X8 (a product of Bio-Rad Laboratories, Richmond, Calif., USA), in acetate form. The eluate is concentrated by evaporation in vacuo and the residue is subjected to counter-current distribution over 785 stages in the system tert.-amyl alcohol/acetic acid/water/toluene (4:2:5:0.8). The phases contained in the units 360 to 400 (K=0.8) are collected, concentrated by evaporation in vacuo and lyophilised from tert.-butanol/water (1:1).

The resulting title compound is uniform in two systems according to thin layer chromatography.

TLC: system 157: $R_f$ 0.35; 157 G: $R_f$ 0.30

The peptide starting material can be obtained in the following manner:

Stage 2.1 Z-Orn(Boc)-Phe-Phe-OTmse 1.47 g of Z-Orn(Boc)-OH, 1.8 g of HCl.H-Phe-Phe-OTmse, 900 mg of DCCI and 645 mg of 1-hydroxybenzotriazole are taken up in 30 ml of dimethylformamide, 0.51 ml of N-ethylmorpholine are added and the mixture is left to stand for 24 hours. It is filtered, the filtrate is concentrated by evaporation and the residue is recrystallised from ethyl acetate. M.p. 147° to 148°.

TLC: system (toluene/acetone 7:3): $R_f$ 0.40.

Stage 2.2 Z-Orn(Boc)-Phe-Phe-OH 1.52 g of Z-Orn(Boc)-Phe-Phe-OTmse (stage 2.1) and 1.85 g of tetraethylammonium fluoride are dissolved in 28 ml of dimethylformamide and the solution is left to stand for 45 minutes. 2 ml of 1N hydrochloric acid and 100 ml of water are then added, and the mixture is filtered and the residue is dried over phosphorus pentoxide.

TLC: system 157 B: $R_f$ 0.45

Stage 2.3
Z-Orn(Boc)-Phe-Phe-(D-Trp)-Lys(Boc)-Thr(But)-Phe-OTmse 278 mg of 1-hydroxybenzotriazole and 412 mg of DCCI are added to a solution of 1.2 g of Z-Orn(Boc)-Phe-Phe-OH (stage 2.2) and 1.52 g of H-(D-Trp)-Lys(Boc)-Thr(But)-Phe-OTmse in 25 ml of dimethylformamide and the whole is left at room temperature for 15 hours. For working up, the precipitated dicyclohexylurea is removed by filtration and the filtrate is concentrated by evaporation in a high vacuum. The oily residue is triturated with 10 ml of methanol and filtered with suction. The undissolved material, in order to be purified, is triturated again with 10 ml of methanol at 50°, filtered with suction, washed with methanol and in vacuo. The product is uniform according to TLC.

TLC: [chloroform/methanol (95:5)]: $R_f$ 0.50

Stage 2.4
Z-Orn(Boc)-Phe-Phe-(D-Trp)-Lys(Boc)-Thr(But)-Phe-OH 2.84 g of Z-Orn(Boc)-Phe-Phe-(D-Trp)-Lys(Boc)-Thr(But)-Phe-OTmse (stage 2.3) are dissolved in 70 ml of a freshly produced anhydrous 0.15M tetraethylammonium fluoride solution in dimethylformamide and maintained at 25° for 30 minutes. After the reaction mixture has cooled to 5°, 1.8 ml of 1N aqueous hydrochloric acid are added while stirring well and the product is precipitated by the addition of 500 ml of water. The material which has been filtered off is washed with water, dried in vacuo over phosphorus pentoxide and further used directly.

TLC: system 157 B: $R_f$ 0.50

Stage 2.5
Z-Orn(Boc)-Phe-Phe-(D-Trp)-Lys(Boc)-Thr(But)-Phe-Gaba-OBzl 307 mg of 1-hydroxybenzotriazole, 413 mg of DCCI and 0.273 ml of N-ethylmorpholine are added to a mixture of 2.3 g of Z-Orn(Boc)-Phe-Phe-(D-Trp)-Lys(Boc)-Thr(But)-Phe-OH (stage 2.4) and 796 mg of Gaba-benzyl ester p-toluenesulphonate in 16 ml of dimethylformamide and the mixture is left at room temperature for 20 hours. For working up, 30 ml of ice-cold methanol are added to the mixture and filtration is carried out. The resulting solid, in order to be purified further, is stirred with 15 ml of warm methanol for 10 minutes, the suspension is cooled to 0° and the pure product is filtered off and dried in vacuo.

TLC: system 157 B: $R_f$ 0.80

Stage 2.6
H-Orn(Boc)-Phe-Phe-(D-Trp)-Lys(Boc)-Thr(But)-Phe-Gaba-OH

A solution of 2.6 g of Z-Orn(Boc)-Phe-Phe-(D-Trp)-Lys(Boc)-Thr(But)-Phe-Gaba-OBzl (stage 2.5) in 125 ml of dimethylformamide is, after the addition of 500 mg of palladium-on-carbon (10%), hydrogenated for 6 hours at room temperature and normal pressure. For working up, once the catalyst has been filtered off the solution is concentrated to 2 ml in a high vacuum, and the product is precipitated with 100 ml of peroxide-free ether, filtered off and dried in vacuo. The crude product is subjected to the next stage without being further purified.

TLC: system 157 B: $R_f$ 0.40

Stage 2.7

⌊—Orn(Boc)—Phe—Phe—(D-Trp)—Lys(Boc)—Thr(But)—Phe—Gaba⌋

A solution of 2.08 g of crude H-Orn(Boc)-Phe-Phe-(D-Trp)-Lys(Boc)-Thr(But)-Phe-Gaba-OH (stage 2.6), 2.41 g of 1-hydroxybenzotriazole and 3.24 g of DCCI in 1570 ml of dimethylformamide is maintained at 50° for 20 hours. For working up, the solvent is evaporated off in a high vacuum at approximately 30°, and the residue is triturated with 30 ml of ethyl acetate. The precipitated dicyclohexylurea is removed by filtration, the filtrate is diluted to 200 ml with ethyl acetate, washed three times with 20 ml of 1N aqueous oxalic acid each time and then with water until neutral, dried over sodium sulphate and concentrated by evaporation in vacuo. The crude product, in order to be purified, is chromatographed over a column of 75 g of silica gel (used in chloroform). After a first run of 200 ml of chloroform, 250 ml of chloroform/methanol (95:5) elute 1.36 g of product which is uniform according to thin layer chromatography.

TLC: system 157 B: $R_f$ 0.70

EXAMPLE 3

H—Lys—Lys—Lys⌐
⌜— Lys—Phe—Phe—(D-Trp)—Lys—Thr—Phe—Gaba —⌐;

467 mg of protected octapeptide of the formula

Boc—Lys(Boc)—Lys(Boc)—Lys(Boc)⌐
⌜— Lys—Phe—Phe—(D-Trp)—Lys(Boc)—Thr(But)—Phe—Gaba —⌐ are dissolved at 5° under $N_2$ in 5 ml of a mixture of 89% by volume of trifluoroacetic acid, 10% by volume of water and 1% by volume of thioglycolic acid, the solution is immediately heated to 25° and, after 90 minutes at room temperature under $N_2$, precipitated with 40 ml of ether. The resulting crude trifluoroacetate of the end product is dried in vacuo, dissolved in 5 ml of 1N acetic acid and filtered through 15 ml of anion exchanger, for example AG ®1-X8 (a product of Bio-Rad Laboratories, Richmond, Calif., USA), in acetate form. The eluate is concentrated by evaporation in vacuo and the residue is subjected to countercurrent distribution over 1280 stages in the system tert.-amyl alcohol/acetic acid/water/toluene (4:2:5:0.8). The phases contained in the units 400 to 430 (K=0.48) are collected, concentrated by evaporation in vacuo and lyophilised from tert.-butanol/water (1:1).

The resulting title compound is uniform in two systems according to thin layer chromatography.
TLC 111 B: $R_f 0.1$.
112 A: $R_f 0.2$.

The peptide starting material can be obtained in the following manner:

Stage 3.1 Z-Lys(Boc)-Phe-Phe-OTmse 3.8 g of Z-Lys(Boc)-OH, 4.49 g of HCl.H-Phe-Phe-OTmse, 1.53 g of 1-hydroxybenzotriazole and 2.26 g of DCCI are dissolved in 40 ml of dimethylformamide, 1.26 ml of N-ethylmorpholine are added and the whole is left to stand for 24 hours at 20°. The reaction mixture is filtered, the filtrate is concentrated and the product is precipitated with water. After drying the precipitate over phosphorus pentoxide, the product is re-precipitated from ethyl acetate/petroleum ether.
TLC: system ethyl acetate: $R_f 0.65$

Stage 3.2 Z-Lys(HCl)-Phe-Phe-OTmse 775 mg of Z-Lys(Boc)-Phe-Phe-OTmse (stage 3.1) are dissolved in 25 ml of hydrogen chloride/ethyl acetate (2.4N) and, after one hour at 20°, the solution is concentrated by evaporation. The residue is triturated with ether and dried over potassium hydroxide.
TLC: system 157: $R_f 0.60$

Stage 3.3

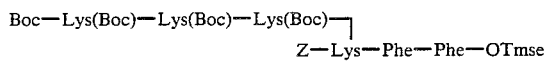

514 mg of Boc-Lys(Boc)-Lys(Boc)-Lys(Boc)-OH (see the following sequence of stages 3.3A-D), 665 mg of Z-Lys(HCl)-Phe-Phe-OTmse (stage 3.2), 157 mg of 1-hydroxybenzotriazole and 212 mg of DCCI are dissolved in 5 ml of dimethylformamide, 0.118 ml of N-ethylmorpholine is added and the mixture is left to stand at 20° for 24 hours. The mixture is filtered, the filtrate is concentrated by evaporation, the residue in 300 ml of ethyl acetate is washed three times with 50 ml of water each time, and the organic phase is dried over sodium sulphate. The solution is concentrated and the product is precipitated with 100 ml of petroleum ether.
TLC: system (chloroform/methanol 93:7): $R_f 0.40$

Stage 3.3A Z-Lys(Boc)-Lys(Boc)-OTmse 0.378 ml of N-ethylmorpholine is added to 1.89 g of Z-Lys(Boc)-OPc and 1.15 g of HCl.H-Lys(Boc)-OTmse in 30 ml of dimethylformamide. After 24 hours at 20° the mixture is concentrated and precipitated with 100 ml of water. The product is dried over phosphorus pentoxide and purified by re-precipitating from ethyl acetate/petroleum ether.
TLC: system (toluene/acetone 7:3): $R_f 0.55$

Stage 3.3B HCl.H-Lys(Boc)-Lys(Boc)-OTmse

After the addition of 130 mg of palladium-on-carbon (10%), a solution of 1.33 g of Z-Lys(Boc)-Lys(Boc)-OTmse (stage 3.3A) in 50 ml of methanol and 1.883 ml of 1N aqueous hydrochloric acid is hydrogenated for one hour at room temperature and normal pressure. The catalyst is filtered off, the solution is concentrated by evaporation and the resulting product is further used directly.
TLC: system 157A: $R_f 0.15$

Stage 3.3C Boc-Lys(Boc)-Lys(Boc)-OTmse 0.285 ml of N-ethylmorpholine and 0.3 ml of isobutyl chlorocarbonate are added to 803 mg of Boc-Lys-(Boc)-OH in 10 ml of dimethylformamide at −15°. After 15 minutes at −15°, a solution of 1.51 g of HCl.H-Lys(Boc)-Lys(Boc;-OTmse (stage 3.3B) and 0.237 ml of N-ethylmorpholine in 15 ml of dimethylformamide is added. After 1 hour at −10° and 24 hours at 20°, the mixture is concentrated by evaporation, and the residue is taken up in 100 ml of ethyl acetate and washed three times with 20 ml of water each time. The organic phase is dried over sodium sulphate, filtered, the filtrate is concentrated and the product is precipitated by the addition of petroleum ether.
TLC: system (toluene/acetone 7:3): $R_f 0.30$

Stage 3.3D Boc-Lys(Boc)-Lys(Boc)-Lys(Boc)-OH 1.5 g of Boc-Lys(Boc)-Lys(Boc)-Lys(Boc)-OTmse (stage 3.3C) and 1.53 g of tetraethylammonium fluoride are dissolved in 20 ml of dimethylformamide. After 45 minutes at 20°, 1.66 ml of 1N aqueous hydrochloric acid and 100 ml of water are added and the mixture is filtered and the residue dried over phosphorus pentoxide.
TLC: system 157B: $R_f 0.40$

Stage 3.4

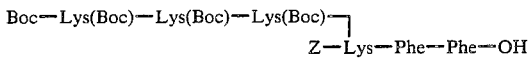

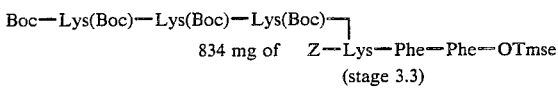

and 530 mg of tetraethylammonium fluoride are left to stand in 7 ml of dimethylformamide for 45 minutes at 20°. 0.571 ml of 1N aqueous hydrochloric acid and 75 ml of water are added, the mixture is filtered and the residue is dried over phosphorus pentoxide.
TLC: system 157B: $R_f 0.40$

Stage 3.5

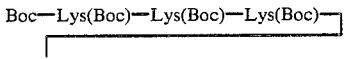

84 mg of 1-hydroxybenzotriazole and 123 mg of DCCI are added to a solution of 740 mg of

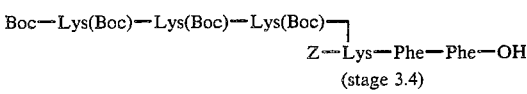

and 455 mg of H-(D-Trp)-Lys(Boc)-Thr(But)-Phe-OTmse in 10 ml of dimethylformamide and the mixture is left at room temperature for 15 hours. For working up, the precipitated dicyclohexylurea is removed by filtration and the filtrate is concentrated by evaporation in a high vacuum. The oily residue is triturated with 5 ml of methanol and filtered with suction. The undissolved material, in order to be purified, is triturated again with 5 ml of methanol at 50°, filtered with suction, washed with methanol and dried in vacuo. The product is uniform according to TLC.

TLC: [chloroform/methanol (9:1)]: R<sub>f</sub> 0.60

Stage 3.6

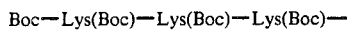
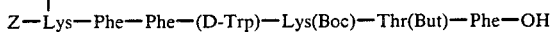

1.04 g of  Z—Lys—Phe—Phe—(D-Trp)—Lys(Boc)—Thr(But)—Phe—OTmse
(stage 3.5)

are dissolved in 25 ml of a freshly produced anhydrous 0.15M tetraethylammonium fluoride solution in dimethylformamide and maintained at 25° for 30 minutes. After cooling to 5°, 0.48 ml of 1N aqueous hydrochloric acid is added the reaction mixture while stirring well and the product is precipitated by the addition of 70 ml of water. The material filtered off is washed with 5 ml of water, dried over phosphorus pentoxide in vacuo and further used directly.

TLC: system 157B: R<sub>f</sub> 0.45

Stage 3.7

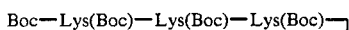

85 mg of 1-hydroxybenzotriazole, 114 mg of DCCI and 0.075 ml of N-ethylmorpholine are added to a mixture of 957 mg of

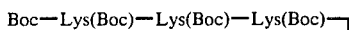
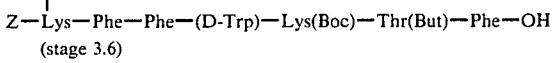
(stage 3.6)

and 219 mg of Gaba-benzyl ester p-toluene sulphonate in 7 ml of dimethylformamide, and the mixture is left at room temperature for 20 hours. For working up, 10 ml of ice-cold methanol are added to the mixture which is then filtered. In order to purify it further, the resulting solid is stirred with 5 ml of warm methanol for 10 minutes, the suspension is cooled to 0°, and the pure product is filtered off and dried in vacuo.

TLC: [chloroform/methanol (9:1)]: R<sub>f</sub> 0.60.

Stage 3.8

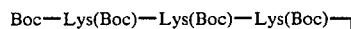
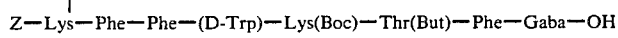

After the addition of 150 mg of palladium-on carbon (10%), a solution of 1.0 g of

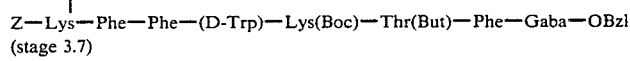
(stage 3.7)

in 50 ml of dimethylformamide is hydrogenated for 6 hours at room temperature and normal pressure. For working up, once the catalyst has been filtered off the solution is concentrated to 2 ml in a high vacuum and the product is precipitated with 50 ml of peroxide-free ether, filtered off and dried in vacuo. The crude product is subjected to the next stage without being further purified.

TLC: system 157A: R<sub>f</sub> 0.30

Stage 3.9

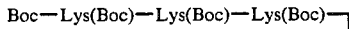

A solution of 913 mg of crude

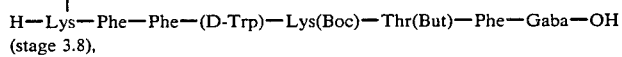
(stage 3.8), 678 mg of 1-hydroxybenzotriazole and 1.0 g of DCCI in 240 ml of dimethylformamide is maintained at 50° for 20 hours. For working up, the solvent is evaporated off in a high vacuum at approximately 30°, and the residue is triturated with 15 ml of ethyl acetate. The precipitated dicyclohexylurea is removed by filtration, the filtrate is diluted to 100 ml with ethyl acetate, washed three times with 20 ml of 1N aqueous oxalic acid each time and then with water until neutral, dried over sodium sulphate and concentrated by evaporation in vacuo. For purification, the crude product is chromatographed over a column of 30 g of silica gel (using chloroform/methanol 95:5). After a first run of 100 ml, the following 250 ml of chloroform/methanol (95:5) elute the product in a form that is uniform according to thin layer chromatography.

TLC: system (chloroform/methanol 9:1): R$_f$ 0.45

EXAMPLE 4

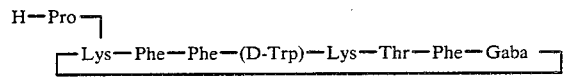

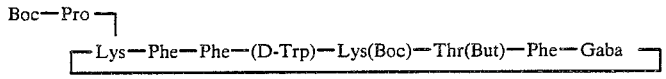

436 mg of protected octapeptide of the formula

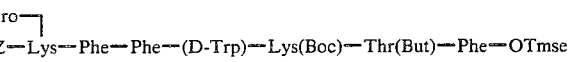

are dissolved at 5° under N$_2$ in 4 ml of a mixture of 89% by volume of trifluoroacetic acid, 10% by volume of water and 1% by volume of thioglycolic acid, the solution is immediately heated to 25° and, after 90 minutes at room temperature under N$_2$, precipitated with 40 ml of ether. The resulting crude trifluoroacetate of the end product is dried in vacuo, dissolved in 5 ml of 1N acetic acid and filtered through 15 ml of anion exchanger, for example AG ®1-X8 (a product of Bio-Rad Laboratories, Richmond, Calif., USA) in acetate form. The eluate is concentrated by evaporation in vacuo and the residue is subjected to countercurrent distribution over 260 stages in the system tert.-amyl alcohol/acetic acid/water/toluene (4:2:5:0.8). The phases contained in the units 66 to 97 (K=0.45) are collected, concentrated by evaporation in vacuo and lyophilised from tert.-butanol/water (1:1).

The resulting title compound is uniform in two systems according to thin layer chromatography.

TLC: system 157: R$_f$ 0.95. system 157A: R$_f$ 0.20.

The peptide starting material can be obtained in the following manner:

Stage 4.1

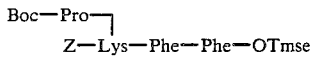

540 mg of Boc-Pro-OH, 1.78 g of Z-Lys(HCl)-Phe-Phe-OTmse, 620 mg of DCCI and 385 mg of 1-hydroxybenzotriazole are taken up in 10 ml of dimethylformamide, 0.319 ml of N-ethylmorpholine are added and the mixture is left to stand for 24 hours at 20°. The mixture is filtered, and the filtrate is concentrated to approximately 2 ml and precipitated with 50 ml of water. After drying the precipitate over phosphorus pentoxide, the product is purified by re-precipitating from ethyl acetate/petroleum ether.

TLC: system (toluene/acetone 7:3): R$_f$ 0.25

Stage 4.2

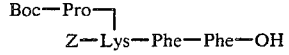

960 mg of 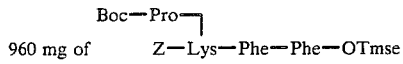

and 1.02 g of tetraethylammonium fluoride are left to stand in 10 ml of dimethylformamide for 45 minutes. Then, 1.1 ml of 1N aqueous hydrochloric acid and 100 ml of water are added, the mixture is filtered, and the residue is washed with water and dried over phosphorus pentoxide.

TLC: system 157A: R$_f$ 0.30.

Stage 4.3

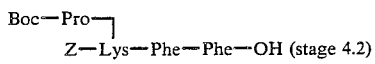

168 mg of 1-hydroxybenzotriazole and 250 mg of DCCI are added to a solution of 810 mg of Boc—Pro—
      |
Z—Lys—Phe—Phe—OH (stage 4.2)

and 921 mg of H-(D-Trp)-Lys(Boc)-Thr(But)-Phe-OTmse in 20 ml of dimethylformamide and the mixture is left for 15 minutes at room temperature. For working up, the precipitated dicyclohexylurea is removed by filtration and the filtrate is concentrated by evaporation in a high vacuum. The oily residue is triturated with 5 ml of methanol and filtered with suction. For purification, the undissolved material is triturated again with 5 ml of methanol at 50°, filtered with suction, washed with methanol and dried in vacuo. The product is uniform according to TLC.

TLC: [chloroform/methanol (9:1)]: R$_f$ 0.45.

Stage 4.4

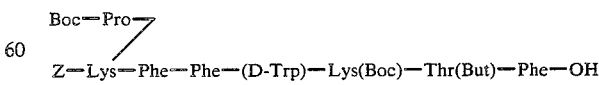

1.49 g of

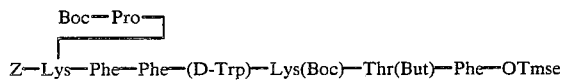

-continued
(stage 4.3)

are dissolved in 45 ml of a freshly produced anhydrous 0.15M tetraethylammonium fluoride solution in dimethylformamide and maintained at 25° for 30 minutes.

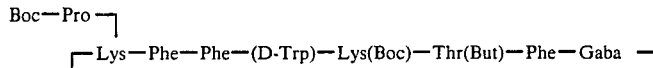

After cooling to 5°, 0.94 ml of 1N aqueous hydrochloric acid are added to the reaction mixture while stirring well and the product is precipitated by the addition of 200 ml of water. The material filtered off is washed with water, dried in vacuo over phosphorus pentoxide and further used directly.
TLC: system 157B: R$_f$0.45.

Stage 4.5

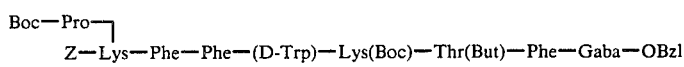

164 mg of 1-hydroxybenzotriazole, 22 mg of DCCI and 0.146 ml of N-ethylmorpholine are added to a mixture of 1.33 g of

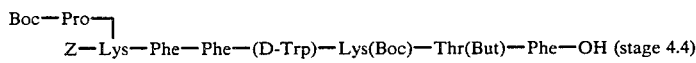

and 425 mg of Gaba-benzyl ester p-toluenesulphonate in 10 ml of dimethylformamide and the mixture is left at room temperature for 20 hours. For working up, 50 ml of ice-cold methanol are added to the mixture which is then filtered. In order to be purified further, the solid obtained is stirred with 15 ml of warm methanol for 10 minutes, the suspension is cooled to 0°, and the pure product is filtered off and dried in vacuo.
TLC: [chloroform/methanol (9:1)]: R$_f$0.60

Stage 4.6

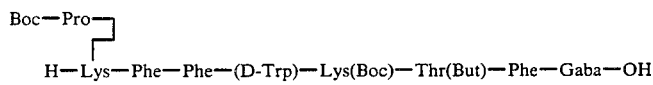

After the addition of 300 mg of palladium-on-carbon (10%), a solution of 1.26 g of

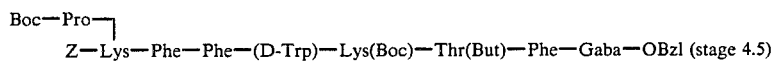

in 100 ml of methanol is hydrogenated for 6 hours at room temperature and normal pressure. For working up, after filtering off the catalyst the solution is concentrated by evaporation and the product is precipitated with 25 ml of peroxide-free ether, triturated and dried in vacuo. The crude product is subjected to the next stage without being further purified.
TLC: system 157B: R$_f$0.25

Stage 4.7

A solution of 1.09 g of crude

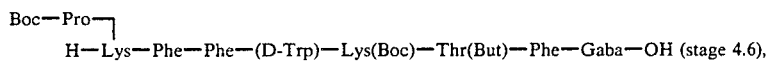

1.16 g of 1-hydroxybenzotriazole and 1.56 g of DCCI in 760 ml of dimethylformamide is maintained at 50° for 20 hours. For working up, the solvent is evaporated off in a high vacuum at approximately 30°, and the residue is triturated with 40 ml of ethyl acetate. The precipitated dicyclohexylurea is removed by filtration, the filtrate is diluted to 200 ml with ethyl acetate, washed three times with 20 ml of 1N aqueous oxalic acid each time and then with water until neutral, dried over sodium sulphate and concentrated by evaporation in vacuo. For purification, the crude product is chromatographed over a column of 30 g of silica gel (using chloroform). After a first run of 300 ml of chloroform, 150 ml of chloroform/methanol (95:5) elute the substance in a form that is uniform according to thin layer chromatography.
TLC: system (chloroform/methanol 93:7): R$_f$0.27

EXAMPLE 5

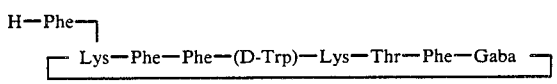

665 mg of protected octapeptide of the formula

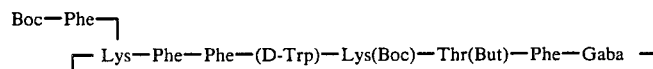

is dissolved at 5° under N₂ in 5 ml of a mixture of 89% by volume of trifluoroacetic acid, 10% by volume of water and 1% by volume of thioglycolic acid, the solution is immediately heated to 25° and, after 90 minutes at room temperature under N₂, precipitated with 30 ml of ether. The resulting crude trifluoroacetate of the end product is dried in vacuo, dissolved in 5 ml of 1N acetic acid and filtered through 15 ml of anion exchanger, for example AG ®1-X8 (a product of Bio-Rad Laboratories, Richmond, Calif., USA), in acetate form. The eluate is concentrated by evaporation in vacuo and the residue is subjected to countercurrent distribution over 750 stages in the system tert.-amyl alcohol/acetic acid/water/toluene (4:2:5:0.8). The phases contained in the units 430 to 470 (K=1.5) are collected, concentrated by evaporation in vacuo and lyophilised from tert.-butanol/water (1:1).

The resulting title compound is uniform in two systems according to thin layer chromatography.

TLC: system 157: R$_f$0.47. system 157C: R$_f$0.2.

The peptide starting material can be obtained in the following manner:

Stage 5.1

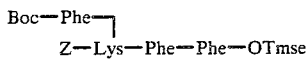

2.65 g of Boc-Phe-OH, 7.11 g of Z-Lys(HCl)-Phe-Phe-OTmse, 2.47 g of DCCI and 1.53 g of 1-hydroxybenzotriazole are taken up in 100 ml of dimethylformamide, 1.275 ml of N-ethylmorpholine are added and the mixture is left to stand at 20° for 24 hours. The mixture is filtered, the filtrate is concentrated to approximately 5 ml and precipitated with 200 ml of water. After drying the precipitate over phosphorus pentoxide, the product is purified by reprecipitating from ethyl acetate/petroleum ether.

TLC: system 157A: R$_f$0.75

Stage 5.2

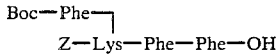

1.82 g of

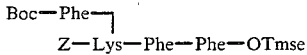

(stage 5.1)

and 1.82 g of tetraethylammonium fluoride are left to stand in 20 ml of dimethylformamide for 45 minutes. Then, 1.96 ml of 1N aqueous hydrochloric acid and 200 ml of water are added, the mixture is filtered, and the residue is washed with water and dried over phosphorus pentoxide.

TLC: system 157A: R$_f$0.30.

Stage 5.3

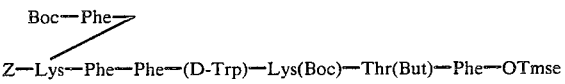

230 mg of 1-hydroxybenzotriazole and 340 mg of DCCI are added to a solution of 1.23 g of

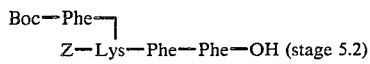 (stage 5.2)

and 1.26 g of H-(D-Trp)-Lys(Boc)-Thr(But)-Phe-OTmse in 20 ml of dimethylformamide and the mixture is left for 15 hours at room temperature. For working up, the precipitated dicyclohexylurea is removed by filtration and the filtrate is concentrated by evaporation in a high vacuum. The oily residue is triturated with 10 ml of methanol and filtered with suction. For purification, the undissolved material is triturated again with 10 ml of methanol at 50°, filtered with suction, washed with methanol and dried in vacuo. The product is uniform according to TLC.

TLC: [chloroform/methanol (93.7)]: R$_f$0.45

Stage 5.4

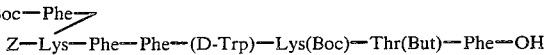

1.8 g of

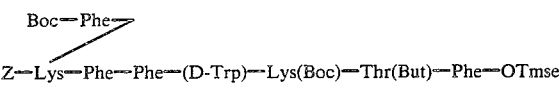

(stage 5.3)

are dissolved in 50 ml of a freshly prepared, anhydrous 0.15M tetraethylammonium fluoride solution in dimethylformamide and maintained at 25° for 30 minutes. After cooling to 5°, 1.1 ml of 1N aqueous hydrochloric acid are added to the reaction mixture while stirring well and the product is precipitated by the addition of 200 ml of water. The material filtered off is washed with water, dried over phosphorus pentoxide in vacuo and further used directly.

TLC: system 157A: R$_f$0.35

Stage 5.5

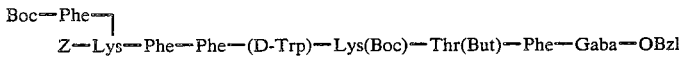

183 mg of 1-hydroxybenzotriazole, 247 mg of DCCI and 0.164 ml of N-ethylmorpholine are added to a mixture of 1.54 g of

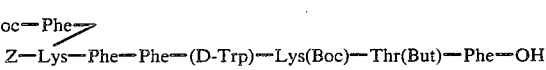

(stage 5.4)

and 476 mg of Gaba-benzyl ester p-toluenesulphonate in 10 ml of dimethylformamide and the mixture is left at room temperature for 20 hours. For working up, 50 ml of ice-cold methanol are added to the mixture which is then filtered. In order to be purified further, the resulting solid is stirred with 5 ml of warm methanol for 10 minutes, the suspension is cooled to 0°, and the pure product is filtered off and dried in vacuo.

TLC: [chloroform/ethanol (93:7)]: R$_f$ 0.50

Stage 5.6

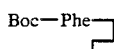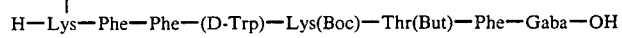

After the addition of 150 mg of palladium-on-carbon (10%), a solution of 1.2 g of

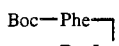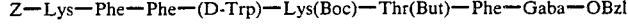

(stage 5.5)

in 60 ml of dimethylformamide is hydrogenated for 6 hours at room temperature and normal pressure. For working up, after filtering off the catalyst the solution is concentrated to 2 ml in a high vacuum and the product is precipitated with 25 ml of peroxide-free ether, filtered off and dried in vacuo. The crude product is subjected to the next stage without being further purified.

TLC: system 157B: R$_f$ 0.30

Stage 5.7

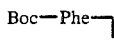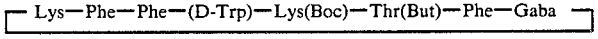

A solution of 1.12 g of

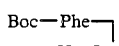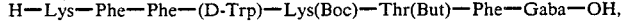

(stage 5.6)

1.07 g of 1-hydroxybenzotriazole and 1.44 g of DCCI in 700 ml of dimethylformamide is maintained at 50° for 20 hours. For working up, the solvent is evaporated off in a high vacuum at approximately 30° and the residue is triturated with 30 ml of ethyl acetate. The precipitated dicyclohexylurea is removed by filtration, and the filtrate is diluted to 200 ml with ethyl acetate, washed three times with 20 ml of 1N aqueous oxalic acid each time and then with water until neutral, dried over sodium sulphate and concentrated by evaporation in vacuo. In order to be purified, the crude product is chromatographed over a column of 30 g of silica gel (using ethyl acetate). After a first run of 100 ml of ethyl acetate, 250 ml of ethyl acetate/methanol (95:5) elute the product in a form that is uniform according to thin layer chromatography.

TLC: system 157A: R$_f$ 0.52.

The following Examples 6 to 11 illustrate the manufacture of pharmaceutical forms of application. The term "active ingredient" refers to the end products of the formula I obtainable according to the invention, especially to those of Examples 1 to 5 and, more especially, to [Lys$^5$,D-Trp$^8$,Gaba$^{12}$]cyclo-somatostatin(-5-12)octapeptide of Example 1, and [N$^\epsilon$-(H-Lys-Lys-Lys)-Lys$^5$, D-Trp$^8$, Gaba$^{12}$]-cyclo-somatostatin(5-12)-octapeptide of Example 3 and [N$\epsilon$-(H-Pro)-Lys$^5$,D-Trp$^8$, Gaba$^{12}$]-cyclo-somatostatin(15—12)-octapeptide of Example 4.

EXAMPLE 6

(A) An injection solution containing 2.0 mg of active ingredient is obtained in the following manner: 1.0 mg of glacial acetic acid, 0.8 mg of sodium acetate, 8.0 mg of sodium chloride and 2.0 mg of active ingredient are dissolved in 0.7 ml of distilled water and the volume is made up to 1 ml with distilled water. The solution is heated for 20 minutes in an autoclave at 120° C. After sterilisation the pH is 4.5.

(B) An injection solution containing 0.5 mg of the active ingredient is obtained in the following manner: 0.5 mg of active ingredient is dissolved in 0.7 ml of physiological sodium chloride solution and the solution is acidified with 0.1N hydrochloric acid to pH 4.0. The volume is made up to 1 ml with distilled water and the mixture is filtered under sterile conditions.

(C) A preparation, containing 0.5 mg of active ingredient, as a sterile dry substance for injection is obtained in the following manner:

0.5 mg of active ingredient is dissolved in 1 ml of an aqueous solution of 20 mg of mannitol. The solution is filtered under sterile conditions and poured under aseptic conditions into a 2 ml ampoule, deep-frozen and lyophilised. Before use, the lyophilisate is dissolved in distilled water. The solution is administered intramuscularly or intravenously.

EXAMPLE 7

An injection preparation containing 1.0 mg of active ingredient as a polyphosphate suspension is obtained in the following manner:

A solution of 1.0 mg of active ingredient and 9.0 mg of sodium chloride in 0.5 ml of distilled water is mixed with a solution of 2 mg of sodium polyphosphate (Calgon N ®) in 0.5 ml of distilled water. The suspension obtained has the following composition:

| active ingredient | 1.0 mg |
|---|---|
| sodium polyphosphate (Calgon N ®) | 2.0 mg |
| sodium chloride | 9.0 mg |
| distilled water to make up to | 1.0 ml. |

The suspension has a pH of 6.9. It is suitable for intramuscular administration.

EXAMPLE 8

Injection preparation containing 0.5 mg of active ingredient as a depot suspension with dextran sulphate.

0.36 mg of acetic acid, 1.9 mg of sodium acetate trihydrate, 8.0 mg of sodium chloride and 0.5 mg of active ingredient are dissolved in 0.4 ml of distilled water and the volume is made up to 0.5 ml with distilled water. 0.5 ml of a 0.1 % solution of dextran sulphate (molecular weight 500,000) is added to this solution while stirring, a homogeneous precipitate being formed. The suspension obtained has the following composition:

| active ingredient | 0.50 mg |
|---|---|
| dextran sulphate MW 500,000 | 0.50 mg |
| acetic acid 100% | 0.36 mg |
| sodium acetate trihydrate | 1.90 mg |
| sodium chloride | 8.00 mg |
| distilled water to make up to | 1.00 ml. |

The aqueous suspension is suitable for intramuscular and subcutaneous injection.

EXAMPLE 9

Nasal spray 30 mg of finely ground active ingredient are suspended in a mixture of 75 mg of benzyl alcohol and 1.395 g of a mixture of semisynthetic glycerides of saturated fatty acids having from 8 to 12 carbon atoms (for example Miglyol ®812). This suspension is placed in aluminium monobloc containers (content 10 ml) which are then closed with a metering valve, and 6.0 g of a mixture of dichlorodifluoromethane and 1,2-dichloro-1,2,2-tetrafluoroethane (for example Freon ®2/114) in a ratio by volume of 40:60 are added under nitrogen pressure. The aluminium container having a total charge of 7.5 g contains 100 individual doses each containing 0.3 mg of active ingredient. The spray container is so adjusted by means of the valve that a single dose is sprayed by pressing once.

Nasal sprays that contain, instead of the Miglyol ®, the same quantity of isopropyl myristate or isopropyl palmitate or a mixture of glycerol and polyoxyethylene glycol esters of fatty acids having 8 and 10 carbon atoms (for example Labrafac ®WL 1219) are manufactured in the same manner.

EXAMPLE 10

Coated tablets or dragées, containing approximately 45 mg of active ingredient for combined rapid and slow release.

Using customary mixing processes, homogeneous mixtures of the following composition are prepared (quantity for 10,000 units)

Mixture A:

| active ingredient | 200 g |
|---|---|
| lactose, anhydrous, for direct tabletting | 940 g |
| cellulose, microcrystalline | 650 g |
| magnesium stearate | 10 g |
| Mixture B: | |
| active ingredient | 250 g |
| lactose, microcrystalline, for direct tabletting | 400 g |
| hydrogenated castor oil, finely particulate | 50 g |

Coated tablets are pressed from mixtures A and B: first of all, the core with prolonged action, which has a weight of 70 mg and a diameter of 6.5 mm, is pressed from mixture B. To produce the coating with rapid release of the active ingredient, mixture A in a weight of 180 mg is taken, and slightly curved dies with a diameter of 8 mm are used, so that coated tablets of a total weight of 250 mg with 20 mg of active ingredient in a rapidly acting form and 25 mg of active ingredient in the retard form are produced.

The resulting coated tablets are, if desired, covered in batches of 100,000 in a confectioning vessel of 65 cm diameter by means of an automatic spraying unit with a conventional lacquer solution of customary composition.

The temperature of the inlet air is 60° C., and the temperature of the cores is maintained at approximately 25° C. Subsequently, the finished dragées are dried for 12 hours at 30° C.

EXAMPLE 11

Dry-filled capsules containing approximately 100 mg of active ingredient.

A mixture of the following composition (for 10,000 units) is prepared:

| active ingredient | 1000 g |
|---|---|
| corn starch | 300 g |
| lactose, crystalline, average particle size of ca 125 μm | 400 g |
| lactose, finely ground | 200 g |
| calcium stearate | 50 g |

This mixture is further pulverised and homogenised as required. The powder is sieved and dry-filled in portions of 195 mg each into gelatine dry-filled capsules. The finished capsules each contain approximately 100 mg of active ingredient.

I claim:

1. A compound selected from the group consisting of (a) a cyclic octapeptide of the formula:

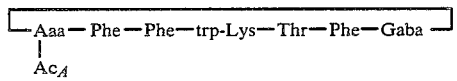

in which

Aaa is the radical of a straight-chained α,ω-diaminoalkanoic acid having from 4 to 7 carbon atoms;

trp is the radical of L-Trp or D-Trp which is unsubstituted or substituted with halogen in the indole nucleus; and $Ac_A$ is bound to the nitrogen of the terminal amino group of Aaa and is (i) hydrogen
(ii) amidino,
(iii) the acyl residue of Lys, Pro or Phe,
(iv) the acyl residue of a di- or tripeptide of lysine.
(b) a therapeutically acceptable salt thereof in which said octapeptide carries a charge and is comprised in the anionic or cationic moiety of the salt, and
(c) a therapeutically acceptable complexes of said octapeptide with a metal compound or a polymeric organic peptide comlex-forming compound.

2. A compound according to claim 1 wherein trp is D-Trp, Aaa is Lys, Orn or Arg, and $Ac_A$ is hydrogen.

3. A compount according to claim 1 wherein trp is D-Trp, Aaa is Lys, Orn or Arg, and $Ac_A$ is a di- or tripeptide of lysine.

4. A cyclic peptide according to claim 1, which is [$Lys^5$,$D-Trp^8$,$Gaba^{12}$]-cyclo-somatostatin(5–12) octapeptide or a physiologically tolerable salt or a thereapeutically acceptable complex thereof.

5. A cyclic peptide according to claim 1, which is [$Orn^5$,$D-Trp^8$,$Gaba^{12}$]-cyclo-somatostatin(5–12) octapeptide or a physiologically tolerable salt or a therapeutically acceptable complex thereof.

6. A cyclic peptide according to claim 1, which is [$N\epsilon$-(Pro)-$Lys^5$,$D-Trp^8$,$Gaba^{12}$]-cyclo-somatostatin-(5–12)-octapeptide or a physiologically tolerable salt or a therapeutically acceptable complex thereof.

7. A cyclic peptide according to claim 1, which is [$N\epsilon$-(Phe)-$Lys^5$,$D-Trp^8$,$Gaba^{12}$]-cyclo-somatostatin-(5–12)octapeptide or a physiologically tolerable salt or a therapeutically acceptable complex thereof.

8. A cyclic peptide according to claim 1, which is [$N\epsilon$-(Lys-Lys-Lys)-$Lys^5$,$D-Trp^8$,$Gaba^{12}$]-cyclo-somatostatin(5–12)-octapeptide or a physiologically tolerable salt or a therapeutically acceptable complex thereof.

9. A therapeutic method for treating conditions responsive to somatostatin in warm-blooded animals comprising administering a somatostatinanalogous cyclooctapeptide according to claim 1 in a preventatively or curatively effective amount to a warm-blooded animal for which such a treatment is indicated.

10. A method according to claim 9 wherein the warm-blooded animal treated is a human.

11. A pharmaceutical composition for the treatment of conditions responsive to somatostatin comprising an effective amount of the cyclic octapeptide according to claim 1, or a physiologically acceptable salt or therapeutically acceptable complex thereof, and a therapeutically acceptable carrier.

* * * * *